United States Patent [19]
Nardella

[11] Patent Number: 5,334,193
[45] Date of Patent: Aug. 2, 1994

[54] FLUID COOLED ABLATION CATHETER

[75] Inventor: Paul C. Nardella, North Easton, Mass.

[73] Assignee: American Cardiac Ablation Co., Inc., Taunton, Mass.

[21] Appl. No.: 975,662

[22] Filed: Nov. 13, 1992

[51] Int. Cl.⁵ .................. A61B 17/39; A61N 1/05
[52] U.S. Cl. .................. 606/41; 607/99; 607/105; 607/113; 607/122
[58] Field of Search .................. 607/98, 99, 101, 102, 607/105, 113, 122, 154, 156; 606/38–41, 34, 45, 48, 49, 50

[56] References Cited

U.S. PATENT DOCUMENTS

| | | | |
|---|---|---|---|
| 3,572,344 | 12/1968 | Bolduc | 128/418 |
| 4,114,623 | 9/1978 | Meinke et al. | 128/303.14 |
| 4,328,806 | 5/1982 | Cooper | 128/349 B |
| 4,474,179 | 10/1984 | Koch | 128/303.17 |
| 4,532,924 | 8/1985 | Auth et al. | 128/303.17 |
| 4,559,951 | 12/1985 | Dahl et al. | 128/642 |
| 4,641,649 | 2/1987 | Walinsky et al. | 128/303.1 |
| 4,785,812 | 11/1988 | Pihl et al. | 128/419 D |
| 4,785,815 | 11/1988 | Cohen | 128/642 |
| 4,805,621 | 2/1989 | Heinze et al. | 128/419 PG |
| 4,869,248 | 9/1989 | Narula | 128/303.13 |
| 4,896,671 | 1/1990 | Cunningham et al. | 128/642 |
| 4,907,589 | 3/1990 | Cosman | 606/34 |
| 4,943,290 | 7/1990 | Rexroth et al. | 606/45 |
| 4,945,912 | 8/1990 | Langberg | 128/642 |
| 4,966,597 | 10/1990 | Cosman | 606/50 |
| 5,006,119 | 4/1991 | Acker et al. | 606/27 |
| 5,156,151 | 10/1992 | Imran | 128/642 |
| 5,168,880 | 12/1992 | Sogawa et al. | 607/102 |
| 5,234,004 | 8/1993 | Hascoet et al. | 607/102 |

Primary Examiner—Lee S. Cohen
Attorney, Agent, or Firm—Lahive & Cockfield

[57] ABSTRACT

A thin, elongate and flexible ablation catheter, suitable for delivery to an internal organ, comprises a fluid delivery lumen centrally located within the catheter, and first and second electrodes disposed on an outer surface of the catheter. The electrodes preferably are helically oriented about the catheter. At least one of the electrodes is in communication with a source of electrosurgical energy so as to deliver ablative electrosurgical energy to tissue. The lumen communicates with a fluid supply source such that fluid is conveyed through the lumen and is discharged to adjacent tissue during the delivery of ablative energy. The fluid delivered through the lumen assists in optimizing the electrode temperature. A method and apparatus is also provided to regulate the fluid flow rate based on monitored electrode temperature and/or tissue impedance.

9 Claims, 3 Drawing Sheets

FLUID COOLED ABLATION CATHETER

BACKGROUND OF THE INVENTION

The invention relates to an electrosurgical device, in the form of a catheter, which is suitable for use in performing tissue ablation. More particularly, the invention features methods and devices to prevent excessive heating of the electrode.

The ablation of selected areas of organ tissue can be performed during surgical procedures to treat disease or medical disorders. Ablation of certain cardiac tissue is performed with increasing frequency to treat certain heart disorders that result in arrhythmia.

The heart is a muscular organ comprising four separate chambers which cooperate to pump blood throughout the body. The heart muscles must contract and relax in a coordinated sequence in order for blood to be passed through the circulatory system in an efficient manner. The heart includes a specialized system for generating impulses to cause rhythmical contraction of the heart muscle and for conducting these impulses rapidly through the heart. In the proper sequence the atria contract about one sixth of a second prior to ventricles. This enables extra filling of the ventricles before they contract to pump blood through the lungs and to other areas of the body.

The rhythmic impulse of the heart is generated in the sinoatrial node (SA node). The SA node has an inherent rhythm which can be modified by the sympathetic and parasympathetic nervous system. The impulse initiated by the SA node spreads through the atrium to the atrioventricular node (AV node), and then through the Purkinje fibers to the endocardial surfaces of the ventricles.

The rhythmical and conduction system of the heart is susceptible to disruption by disease. Damage caused to cardiac tissue can result in the inability of the cardiac conduction pathways to properly transmit the electrical impulses generated in the SA node, leading to arrhythmias, or irregular heartbeats. Cardiac arrhythmias can often be detected through electrocardiograms.

Some forms of cardiac arrhythmia are able to be controlled through medication. However, other forms of arrhythmia do not respond to medication. Moreover, medication typically does not cure the problem, and the dosage and the medication type must be changed periodically to enable continued control of the problem.

One alternative to medication is the surgical removal of a portion of the cardiac pathway which is responsible for the arrhythmia. The many dangers associated with open heart surgery render this a less preferred treatment option. Recently, however, it has become possible to intravascularly insert a specialized catheter within the heart, for positioning adjacent to the conduction tissue responsible for the arrhythmia. The catheter is adapted to deliver energy (e.g., radio frequency energy) to ablate or destroy the tissue responsible for an arrhythmia. This has been found to be a relatively safe and effective technique for eliminating many causes of arrhythmia. Various ablation catheters and techniques for their use are described in U.S. Pat. Nos. 4,641,649; 4,785,815; 4,869,248; and 4,896,671.

Cardiac ablation catheters typically have at least one electrode at the distal end of the catheter which is adapted to deliver energy to the tissue lesion. Other electrodes can be proximally positioned on the catheter and used for sensing endocardial signals. Ablation may be achieved by the application of electrical energy, such as radio frequency (RF) or direct current (DC) energy, from a generator source, through a conductor disposed within the catheter, and to the distal electrode.

During ablation procedures, energy, typically in the form of RF energy, is delivered to tissue by one or more electrodes mounted on an endocardial catheter. The delivery of the RF energy through the electrodes results in an associated temperature rise in the electrodes, and the heat is transferred to adjacent tissue. Although the application of heat to tissue can destroy the tissue (thus eliminating the arrhythmia), it is preferable to have the tissue ablation effected by the application of RF energy. Excess heating of the tissue can prolong the ablation procedure as the energy must be applied intermittently over a longer period of time to prevent an excessive rise in tissue temperature. Moreover, if thermal rather than electrical destruction of tissue is effected it is often not possible to achieve deeper penetration of the energy because the rise in tissue impedance in tissue adjacent the catheter inhibits the delivery of RF energy to deeper tissue. This is most commonly a problem where it is necessary to treat deeper or larger lesions.

It would thus be advantageous to develop an ablation catheter, suitable for use in cardiac ablation procedures, that is able to effectively deliver electrosurgical energy to tissue, without associated excessive heating of the ablation electrode and the adjacent tissue.

It is thus an object of the invention to provide a catheter suitable for use with cardiac ablation procedures utilizing the delivery of radio frequency energy. A further object is to provide an ablation catheter that more effectively delivers radio frequency energy to desired tissue without a significant transfer of heat to tissue from the electrode. Another object of the invention is to provide such an ablation catheter together with a system for controlling the temperature of ablation electrodes. It is also an object of the invention to provide an ablation catheter able to operate in a bipolar mode. Other objects will be apparent upon reading the disclosure which follows.

SUMMARY OF THE INVENTION

The present invention comprises an intravascular ablation catheter and a system for operating the catheter. The system comprises a thin, flexible, elongate catheter member having dimensions suitable for intravascular delivery to an internal organ. Preferably, the elongate catheter member is constructed of a biocompatible, nonconductive material. A fluid conveying lumen is associated with the elongate catheter member, and preferably is disposed within the catheter along the longitudinal axis thereof. The lumen is adapted to communicate with a fluid supply source to convey fluid from the source and through the lumen to be discharged through an outlet port disposed at a distal portion of the member.

The catheter also has at least two electrodes, electrically isolated from one another, that are mounted on the outer surface of the member. A first electrode is adapted to communicate with an electrosurgical generator unit to deliver ablative energy to tissue. A second electrode preferably is a ground electrode that enables the catheter to function in a bipolar mode. In a preferred embodiment the electrodes are helically oriented about the surface of the member.

The catheter of the invention is particularly useful for cardiac ablation procedures. Ablative energy is applied between the two separate electrodes to destroy tissue within the heart responsible for the arrhythmia. While the ablative energy is applied a fluid such as normal saline is delivered through the lumen. The fluid flow through the lumen serves to limit the heat transferred by the energy-delivering electrode to adjacent tissue. Control of the temperature of the energy-delivering electrode enables effective bipolar operation of the catheter utilizing, for example, RF ablation energy.

The invention also comprises a method and system for controlling the flow rate of fluid through the lumen to optimize the cooling of the energy delivering electrode of the catheter. The control system preferably regulates the flow rate based on signals representative of the temperature of the catheter tip and/or tissue impedance.

DETAILED DESCRIPTION OF THE INVENTION

Figure 1:
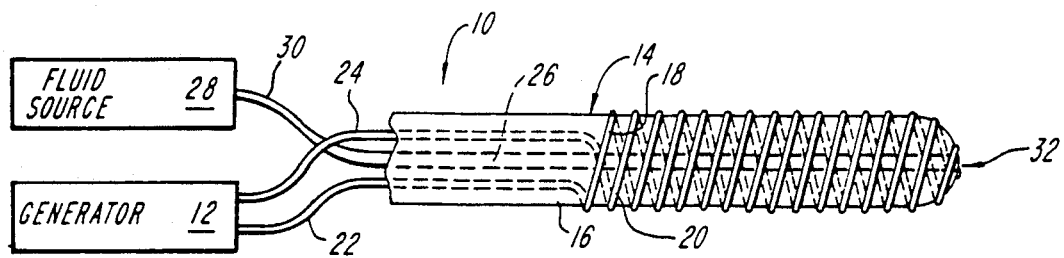
FIG. 1 is a schematic illustration of an ablation catheter and the ablation catheter system of the present invention.

FIG. 1 illustrates an ablation catheter system 10, constructed according to the present invention. The system 10 comprises an electrosurgical generator unit 12 which is able to supply electrosurgical energy to catheter 14. Catheter 14 comprises a thin, flexible, elongate member 16 having first and second electrodes 18, 20 mounted over a distal portion of the outer surface of the member. Electrodes 18, 20 communicate with electrosurgical generator unit 12 through electrode 22, 24. Further, a lumen 26 is disposed within catheter 14, preferably along the longitudinal axis thereof, and is adapted to convey fluid through the catheter. Lumen 26 preferably communicates with a fluid source 28 through conduit 30. Fluid is delivered through the lumen to be discharged through outlet port 32 which is disposed at a distal portion of the catheter. The outlet port 32 preferably is disposed in the distal tip of the electrode.

Figure 2:
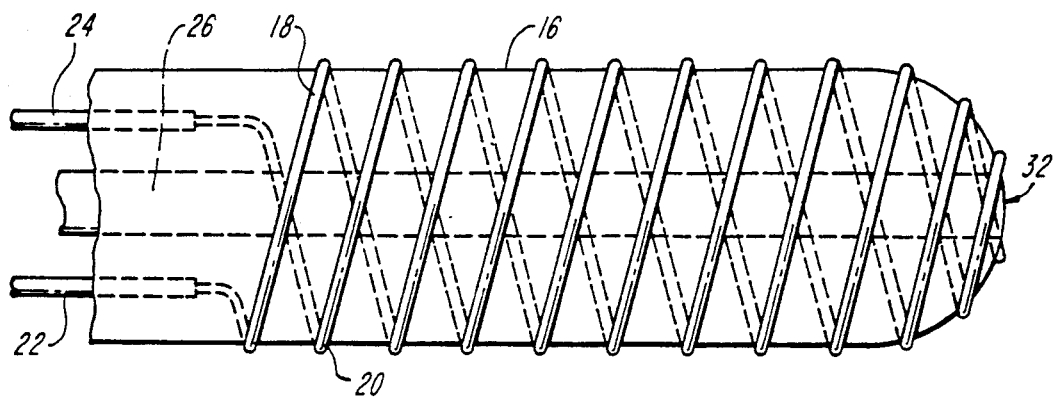
FIG. 2 is a perspective view, partially cut away, illustrating the ablation catheter of FIG. 1.
Figure 3:
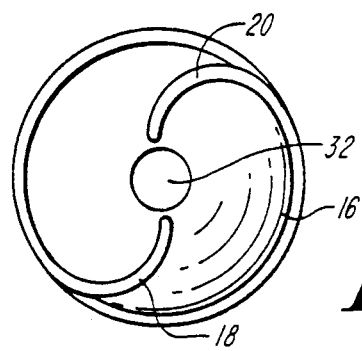
FIG. 3 is a front end view of the ablation catheter of FIG. 1.

Electrodes 18, 20 preferably are helically oriented about the surface of member 16 as illustrated in FIGS. 1 through 3. In a preferred embodiment the electrodes are exposed only over a distal portion of the catheter, for example, over a distance of about 8 centimeters. Conductor leads 22, 24 extend within the catheter and attach to electrodes 18, 20 to convey electrosurgical energy thereto.

The catheter of the system is adapted to perform tissue ablation procedures, and is particularly well suited to perform ablation of tissue that forms cardiac accessory pathways which give rise to arrhythmias. The catheter can also be used to ablate cardiac tissue to remedy other electrical abnormalities, including the causes for ventricular tachycardia. During an ablation procedure the catheter is intravascularly delivered to an organ such as the heart. Upon proper positioning of the catheter adjacent tissue to be ablated, electrosurgical energy, preferably in the radio frequency range, is delivered from generator unit 12 through electrode 18, for example, which may serve as an active, energy-delivering electrode. Electrode 20 preferably functions as a ground electrode to enable bipolar operation of the catheter.

Figure 4:
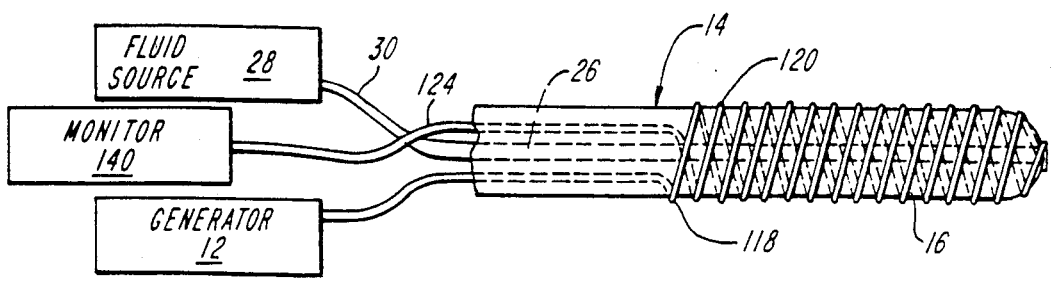
FIG. 4 is a schematic illustration of an alternative ablation catheter and ablation catheter system which operates in a monopolar mode.

In an alternative embodiment, such as illustrated in FIG. 4, the catheter may be one that operates in a monopolar mode, delivering electrosurgical energy from generator unit 12 between electrode 118 and a remote ground plate (not shown). In such an embodiment electrode 120 may be a sensing electrode, which communicates with monitor 140, and which serves to monitor endocardial signals.

During ablation procedures the delivery of electrosurgical energy through electrode 18 tends to increase the temperature of the electrode. Over time, the heat of electrode 18 is transferred to tissue adjacent to the electrode. Such heating of tissue by heat transfer from electrode 18 can be counterproductive in that it can rapidly dehydrate the tissue. Upon dessication of the tissue a significant increase in the impedance of the tissue results, thus inhibiting further delivery of electrosurgical energy to the tissue. As a result, ablation can be less effective and it may be possible to ablate only smaller sized areas of tissue. In order to ablate larger areas of tissue the ablation procedure must be conducted with intermittent energy delivery, causing the procedure to require additional time to complete. The heat transfer from the electrode to the tissue thus limits the effectiveness of the ablation procedure as well as the size of the lesion that can be ablated.

The catheter system of the present invention minimizes the magnitude of heat transfer from electrode 18 to adjacent tissue, and prevents such heat transfer from being a limiting factor in the effectiveness of the ablation procedure. In the present invention lumen 26 delivers a fluid through the member 16 and discharges the fluid through port 32 disposed at the distal portion of member 14. When fluid is delivered through lumen 26 during the application of electrosurgical energy, it tends to lower, or at least maintain, the temperature of the electrodes 18, 20 at a level where heat transfer from the active electrode to adjacent tissue is within acceptable limits. Preferably the fluid conveyed through lumen 26 is normal saline, however other suitable fluids including distilled, deionized water may be used as well. The temperature of the fluid directed through lumen 26 preferably is in the range of about 18° C. to 30° C.

In one embodiment fluid may be continuously conveyed through lumen 26 throughout an ablation procedure. In a preferred embodiment however, the fluid flows through the lumen at a variable rate, and preferably only during the delivery of electrosurgical energy. The flow rate of the fluid can range from about 1 ml per minute to about 100 ml per minute. Preferably, the flow rate is in the range of about 30 to 50 ml per minute, and the fluid is not delivered in the absence of electrosurgical energy delivery.

Preferably, the fluid is effective to maintain the temperature of the electrodes below about 60° C.

As noted, the ablation catheter of the invention possesses dimensions which render it suitable for intravascular delivery to internal organs, particularly the heart. Accordingly, the catheter should have a diameter in the range of 2-14 french to accommodate the intravascular delivery of the catheter. The length of catheter 14 generally is relatively long (e.g. about 3-4 feet) to facilitate intravascular delivery to the heart, for example, from the femoral artery. While the catheter generally is relatively long, the electrodes 18, 20 are typically disposed only over an area which ranges from the distal tip of catheter 14 to about 3 to 5 inches proximal of the distal tip.

The catheter is typically manufactured of flexible, biocompatible materials such as non-conductive polymers. Further, the material should not be thermally insulating and should facilitate effective heat transfer between electrode 18 and fluid in lumen 32. Exemplary polymers from which the catheter can be manufactured are well known in the art and include polyolefins, nylons, polytetrafluoroethylene, polyvinylidene fluoride, and fluorinated ethylene-propylene polymers, and woven dacron with fillers.

As noted, the diameter of the catheter may be within a range which is well known in the art. Generally the catheter diameter 13 in the range of 2 to 14 french. Lumen 26 may have a diameter which ranges from about 1 to 3 french. The ratio of the catheter diameter to lumen diameter can be adjusted by one skilled in the art to optimize the cooling effect of fluid passing through lumen 26. Preferably, this ratio is in the range of 2.5:1 to about 3.5:1.

The catheter may also be constructed to have additional lumens disposed therein. Also, the catheter can have multiple ports disposed in its side surface through which fluid can exit.

Virtually any generator able to provide electrosurgical energy for medical applications may be used with the present invention. Preferably, the generator is a voltage determinative, low source impedance generator which provides radio frequency energy. A suitable generator supplies up to about 2 amps of current and has an impedance value of less than 10 ohms.

Although virtually any frequency in the RF range may be supplied to the ablation catheter 16, the preferred range is about 500 to 700 KHz, and most preferably about 550 KHz. The power delivered is about 20 to 50 W.

The energy requirements of the ablation catheter are dynamic and may vary depending upon the impedance value of the tissue at any time during the treatment. The impedance of tissue varies among tissue types and the amount of blood present in or around the tissue. The amount of current delivered by electrodes 18 or 20 to the tissue thus depends on the impedance of the tissue. Where the tissue contacted has a lower impedance value, more current will be delivered to the tissue through the electrodes. Conversely, less current will be delivered where the tissue has a higher impedance value. The current delivered during ablation procedures by catheter 16 is known in the art and generally ranges between 0.1 and 0.75 amps. The voltage applied to the tissue between the electrodes for such ablation procedures is also known and generally ranges between about 50 to 300 volts rms, and more preferably about 45 to 60 volts rms.

The switching mechanism or mechanisms used to control the delivery of electrosurgical energy to the catheter can be of any type well known in the art. One having ordinary skill in the art will readily understand the most desirable type of switching mechanism to be used for a particular application.

Fluid source 28 may comprise a fluid reservoir having a pump and/or valve mechanism (not shown) to control or regulate the flow of fluid. A switching mechanism separate from that used to control the delivery of electrosurgical energy may be used to control the flow of fluid through lumen 26. Alternatively, the flow of fluid may be coupled to the delivery of electrosurgical energy such that when energy is applied, the pump and/or valve are also activated so as to convey fluid through conduit 30 and lumen 26. The various alternatives which may be utilized to deliver the fluid from source 28 through lumen 26 will be well understood by those having ordinary skill in the art.

In a preferred embodiment, as noted above, one of electrodes 18, 20 serves as an active, energy delivering electrode while the other serves as a ground electrode. In an alternative embodiment illustrated in FIG. 4, electrode 118 still serves as the active, energy delivering electrode. However, electrode 120 communicates via electrical lead 124 with a monitor apparatus 140. In this configuration electrode 120 serves as a sensing electrode, of the type well known in the art, which in combination with monitor 140, detects endocardial signals to assist in the placement of catheter 16 within the heart.

The electrodes 18, 20 preferably are manufactured of highly conductive, biocompatible materials of the type well known in the art. Exemplary materials from which the electrodes can be constructed includes gold, silver and platinum. The electrodes may be formed of a solid material, or they may be formed by plating conductive materials upon a non-conductive substrate such as a polymer.

Fluid flow through the catheter, as noted above, is effective to prevent excessive heating of energy delivering electrodes 18 or 20. Preferably, the flow rate is variable and is dependent on monitored electrode temperature and/or tissue impedance values. In a preferred embodiment tissue impedance may be monitored continuously. If the monitored impedance exceeds a predetermined set point, a disabling signal can be transmitted to generator unit 12, causing delivery of current to cease. At the same time electrode temperature can be monitored and compared to a temperature set point. Fluid flow can be increased or decreased, as necessary, to maintain the monitored electrode temperature at or below the set point. It is understood that fluid flow rate may also be controlled by monitoring tissue impedance alone, or by monitoring electrode temperature alone. In another embodiment it is possible to use the monitored impedance and/or electrode temperature values to control the output power of generator unit 12. Such a technique can also assist in preventing excessive heating of tissue.

Figure 5:
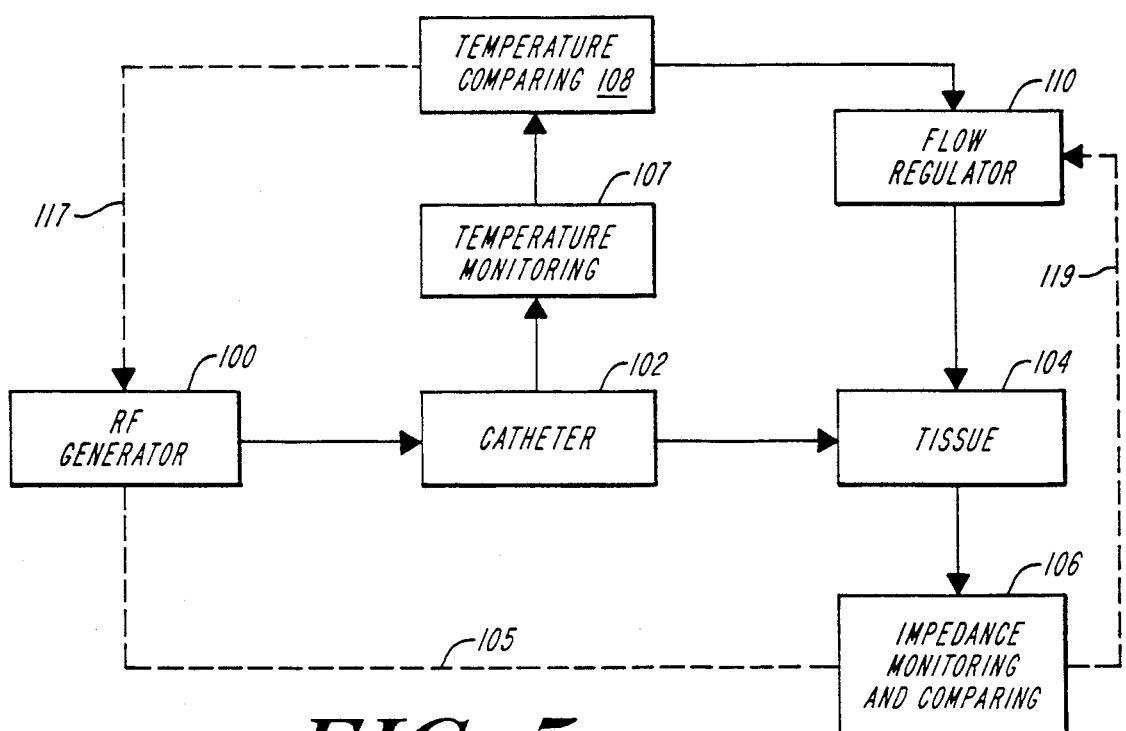
FIG. 5 is a block diagram illustrating a feedback system useful to control the temperature of energy delivering electrodes.

FIG. 5 illustrates a block diagram that is representative of the temperature/impedance feedback system useful to control fluid flow rate through the catheter. Energy, such as RF energy, is delivered to catheter 102 from generator unit 100, and applied to tissue 104. Monitor 106 ascertains tissue impedance, based on the energy delivered to tissue, and compares the measured impedance value to a set value. If the measured impedance exceeds the set value a disabling signal 105 is transmitted to generator 100, ceasing further delivery of energy to the catheter 102. Assuming the measured impedance is within acceptable limits energy continues to be applied to the tissue. During the application of energy to tissue a temperature sensing element 107 (such as a thermistor, thermocouple, or the like) measures the temperature of the energy delivering electrodes. Comparator 108 receives a signal representative of the measured temperature and compares this value to a pre-set signal representative of the desired temperature. Comparator 108 communicates a signal to flow regulator 110 representing the need for a higher flow rate (if electrode temperature is high) or to maintain flow rate (if the temperature is adequate).

Further, output 117 from temperature comparator 108 can be input to generator 100 to regulate the amount of power delivered by the generator, thus controlling temperature. Similarly, output 119 from impedance monitor and comparator 106 can be input to flow regulator 110 to regulate fluid flow and thus control electrode temperature.

Figure 6:
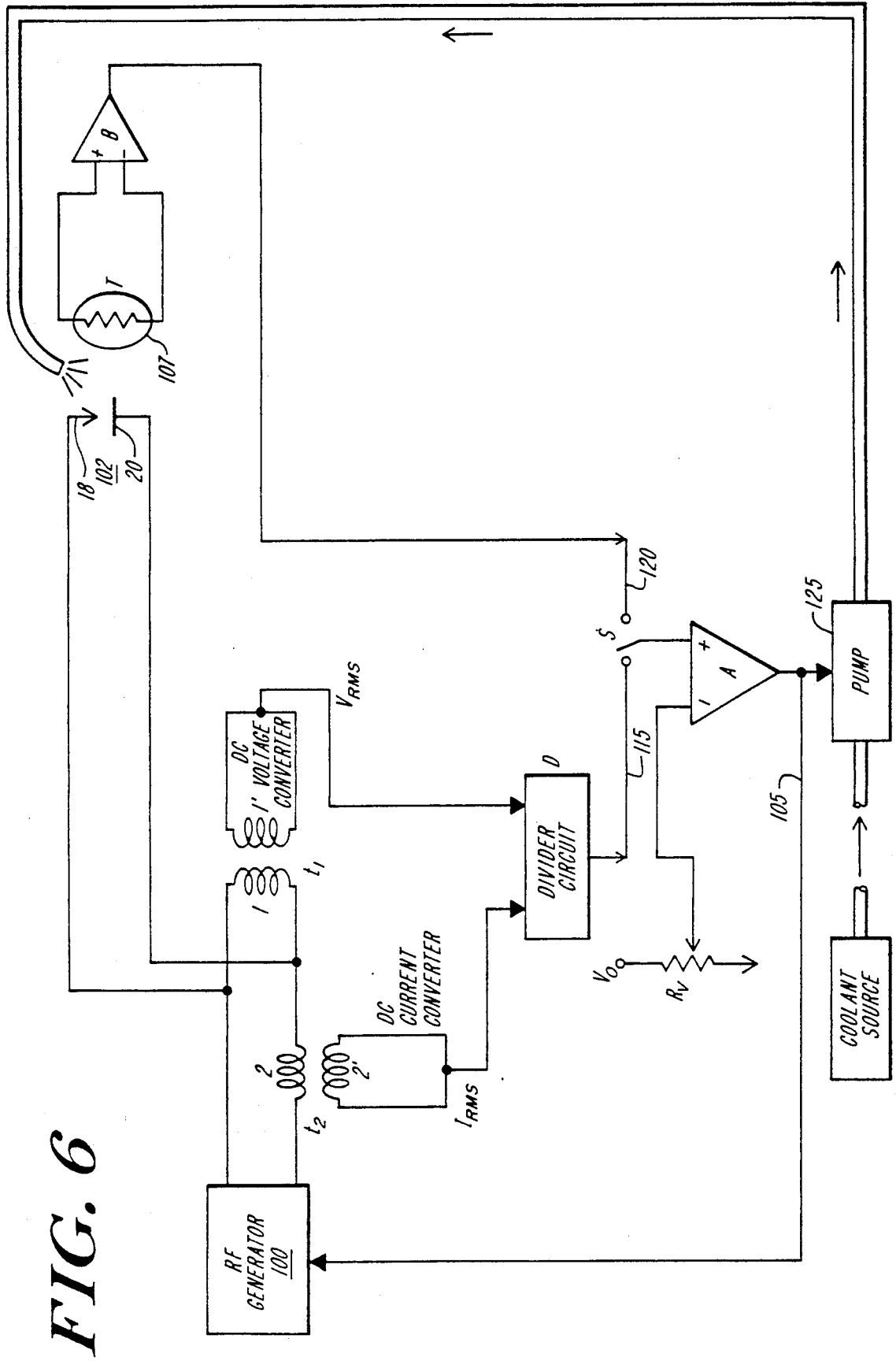
FIG. 6 illustrates a circuit useful to implement the feedback system of FIG. 5.

One or ordinary skill in the art will readily appreciate that the feedback system illustrated in FIG. 5 can be implemented in a variety of ways. FIG. 6 illustrates a circuit useful to facilitate the feedback system.

As shown in FIG. 6 an energy delivering means, such as RF generator 100, is transformer coupled to the catheter 102, to apply a biologically safe voltage to a patient's tissue. In this embodiment, the catheter is represented as a bipolar ablation catheter 102 having an energy delivering electrode 18 and a ground electrode 20. Both electrodes 18,20 are connected to the primary side of the transformer windings 1,2. The common primary winding 1,2 is magnetically coupled via a transformer core to the secondary windings 1',2' so that the current and voltage of the primary side is reflected to the secondary windings 1',2'.

According to a preferred aspect of the invention, the primary windings 1 of the first transformer $t_1$ couple the output voltage of the catheter 102 to the secondary windings 1'. The primary windings 2 of the second transformer $t_2$ couple the output current of the catheter 102 to the secondary windings 2'. Those of ordinary skill in the art will appreciate that the two transformers act as step-down transformers and further serve as means of isolating the high voltage between the catheter 102 and the secondary windings or measuring circuit 1',2'.

The measuring circuits determine the root mean square (RMS) values or magnitudes of the current and voltage and these values, represented as voltages, are inputted to a dividing circuit D to geometrically calculate, by dividing the RMS voltage value by the RMS current value, the impedance of the body tissue at the catheter electrode 102. Those of ordinary skill in the art will understand that the voltage presented at the output of the divider circuit D is representative of and a function of the impedance of the tissue adjacent to the catheter electrodes 18,20.

The output voltage of the divider circuit D is presented at the positive(+) input terminal of comparator A. A voltage source $V_o$ supplies a voltage across the variable resistor $R_v$, thus allowing one to manually adjust, via a knob, the voltage presented at the negative input of comparator A. This voltage represents a maximum impedance value beyond which power will not be applied to the catheter 102. Specifically, once the tissue is heated to a temperature corresponding to an impedance value greater than the maximum cut-off impedance, the RF generator 100 will stop supplying power to the catheter 102. Comparator A can be of any of a commercially available type that is able to control the amplitude or pulse width modulation of the RF generator 100.

In one aspect of the invention, the flow rate of the coolant can be controlled based on the tissue impedance, as represented by signal 115, or based on the catheter temperature, as represented by signal 120. In one embodiment, the switch S is activated to allow the impedance signal 115 to enter the positive(+) input terminal of comparator A. This signal along with the reference voltage applied to the negative(−) input terminal actuates the comparator A to produce an output signal. If the tissue is heated to a biologically damaging temperature, the tissue impedance will exceed the selected impedance value seen at the negative(−) input terminal thereby generating a signal 105 to disable the RF generator 100, ceasing the power supplied to the catheter 102.

The output signal of comparator A can further be communicated to pump 125. If the temperature of the ablation catheter 102 is high, despite the tissue impedance falling within acceptable limits, the pump 125 will adjust the rate of flow of the cooling fluid subsequently applied to the catheter electrodes 18, 20 to decrease the catheter temperature. Thus, the output signal of comparator A may either disable the RF generator's 100 power output (depending on the tissue temperature as reflected by its impedance) or cool the ablation catheter or perform both operations simultaneously.

In another aspect of the invention, the rate of flow of the cooling fluid is controlled based on the electrode temperature measured at the catheter tip. The switch S is actuated so as to transfer to the positive(+) input terminal of comparator A the comparator B output signal 120. The temperature sensor can be a thermistor T, disposed or adjacent the catheter 102. The thermistor T senses temperature and reacts to differential temperature changes in a predictable manner. Thus, the thermistor actively reflects through varying resistance the temperature it is exposed to.

Both leads of the temperature sensitive thermistor T are inputted to the positive(+) and negative(−) terminals of comparator B to produce a signal 120 indicative of the catheter temperature. This signal 120 works in conjunction with the reference voltage inputted at the negative(−) terminal to activate the comparator A to produce an output signal that is electrically communicated to the pump 125. The pump 125, in response to the signal, selectively varies the flow rate of the cooling fluid within lumen 26.

It is understood that the temperature of the electrode can be continuously monitored or randomly sampled to ensure against excessive heating of the tissue. Moreover, the pump employed can be a valve, or series thereof, rather than an electrical-mechanical apparatus. The valve can adjust the rate of flow of the cooling liquid from the fluid supply source in the same manner as a pump.

Various modifications may be made in the invention without departing from the intended scope of the claims. For example, the outlet port through which fluid is discharged need not be disposed at the distal tip of the catheter member and may instead be disposed in a side wall of the catheter.

What is claimed is:

1. A method for controlling the temperature of an energy delivering electrode disposed on an ablation catheter, comprising:

providing an ablation catheter in the form of a thin, flexible elongate member having disposed at a distal portion thereof at least one energy delivering electrode, the catheter having a fluid delivering lumen associated therewith and being adapted for intravascular delivery to an internal organ and being in electrical communication with an electrosurgical generator unit;

intravascularly delivering the catheter to an internal organ;

delivering electrosurgical energy from the generator unit through the catheter to the energy delivering electrode and adjacent tissue;

measuring the temperature of the energy delivering electrode and generating a signal representative thereof;

comparing the measured temperature of the energy delivering electrode to a predetermined maximum temperature value and generating a signal representative of the difference between the measured temperature and the predetermined temperature;

selectively delivering fluid through the lumen of the catheter at a desired flow rate; and adjusting the flow rate of fluid through the lumen of the catheter based on the difference between measured temperature and the predetermined temperature to maintain the measured temperature at or below the predetermined temperature.

2. The method of claim 1 wherein the step of selectively delivering fluid further comprises the step of allowing the fluid to exit the catheter at a distal thereof.

3. The method of claim 2 wherein the flow rate is adjusted by a pump means for controlling fluid flow rate that operates in response to a signal representative of the difference between the measured temperature and the predetermined temperature.

4. The method of claim 1 wherein the fluid flow rate ranges from 1 to 50 ml/minute.

5. The method of claim 1 further comprising the step of controlling an amount of electrosurgical energy delivered by the generator unit in conjunction with controlling the temperature of the energy delivering electrode by:

measuring the impedance of the tissue based on the energy applied thereto and generating a signal representative of the measured tissue impedance value;

comparing the measured tissue impedance value with a predetermined maximum impedance value; and transmitting to the generator unit a signal to cease further energy delivery if the measured tissue exceeds the predetermined maximum impedance value.

6. A system for controlling the temperature of an energy delivering electrode disposed on an ablation catheter, comprising:

a thin, flexible elongate catheter having a central lumen disposed therein to enable fluid to be conveyed through the catheter, at a variable rate of flow, for discharge at a distal portion of the catheter, the catheter having at least one energy delivering electrode disposed at a distal portion of the catheter and the catheter having dimensions suitable for intravascular delivery;

an electrosurgical generator unit in electrical communication with the catheter for providing a desired electrosurgical energy output to the electrode for delivery to tissue adjacent the electrode;

a fluid supply source in communication with the lumen;

temperature sensing means associated with the catheter for sensing the temperature of the energy delivering electrode and generating a signal representative of measured electrode temperature;

comparator means for comparing the measured electrode temperature and a predetermined maximum temperature value and generating a signal representative of the temperature difference; and a fluid control means for regulating the rate of flow of fluid through the lumen in response to the signal from the comparator means representative of the temperature difference to maintain the measured electrode temperature at or below the predetermined temperature.

7. The system of claim 6 wherein the temperature sensing means comprises a thermistor or a thermocouple.

8. The system of claim 6, further comprising a subsystem for controlling the electrosurgical energy output of the generator unit, the subsystem comprising:

impedance measuring means for measuring the impedance value of tissue based on the energy applied thereto;

impedance comparing means for comparing the measured impedance value of tissue to a predetermined maximum impedance value, the impedance comparing means generating a disabling signal if the measured impedance value exceeds the predetermined maximum impedance value; and means for communicating the disabling signal to the generator unit to cease further delivery of energy from the generator unit to the catheter.

9. A system for controlling the temperature of an energy delivering electrode disposed on an ablation catheter, comprising:

a thin, flexible elongate catheter having a central lumen disposed therein to enable fluid to be conveyed through the catheter, at a variable flow rate, for discharge at a distal portion of the catheter, the catheter having at least one energy delivering electrode disposed at a distal portion of the catheter and the catheter having dimensions suitable for intravascular delivery;

an electrosurgical generator unit in electrical communication with the catheter for supplying electrosurgical energy to the electrode for delivery to tissue adjacent the electrode;

a fluid supply source in communication with the lumen;

impedance measuring mean for measuring the impedance value of tissue based on the energy applied thereto;

impedance comparing means for comparing the measured impedance value of tissue to a predetermined maximum impedance value, the impedance comparing means generating a signal representative of the difference between the measured impedance value and the predetermined maximum in impedance value; and a fluid control means for regulating the rate of flow of fluid through the lumen in response to the signal from the impedance comparing means representative of the impedance difference to maintain the measured impedance value at or below the predetermined maximum impedance value.

* * * * *